United States Patent [19]

Hujar et al.

[11] Patent Number: 5,557,807
[45] Date of Patent: Sep. 24, 1996

[54] HEADWEAR INCLUDING COOLANT MEANS

[76] Inventors: Jerry Hujar, 1009 Melrose St., Seffner, Fla. 33584; Duelda Hujar, 1511 Broker Rd., Brandon, Fla. 33511

[21] Appl. No.: 328,372

[22] Filed: Oct. 25, 1994

[51] Int. Cl.$^6$ .............................. A42B 1/02; A42B 1/18
[52] U.S. Cl. ................................ 2/171.2; 2/7; 2/209.13
[58] Field of Search .................................. 607/109, 110, 607/114; 2/181, 171.2, 7, 195.1, 209.13, 174, 200.1

[56] References Cited

U.S. PATENT DOCUMENTS

| | | | |
|---|---|---|---|
| 3,070,803 | 1/1963 | Slepicka | 2/7 |
| 4,180,868 | 1/1980 | Snow | 2/7 |
| 4,190,054 | 2/1980 | Brennan | 607/109 |
| 4,237,558 | 12/1980 | Mackenroth, III et al. | 2/7 |
| 4,356,709 | 11/1982 | Alexander | 607/109 |
| 4,530,220 | 7/1985 | Nmabu et al. | 62/530 |
| 4,815,144 | 3/1989 | Martin | 2/181 |
| 5,054,122 | 10/1991 | Sher | 2/7 |
| 5,086,629 | 2/1992 | Dibrell | 128/403 |
| 5,088,487 | 2/1992 | Turner | 128/402 |
| 5,150,707 | 9/1992 | Anderson | 128/402 |
| 5,197,292 | 3/1993 | McPherson | 2/7 |
| 5,305,470 | 4/1994 | McKay | 2/171.2 |
| 5,327,585 | 7/1994 | Karlan | 2/171.2 |

*Primary Examiner*—Amy B. Vanatta
*Attorney, Agent, or Firm*—Dominik & Stein

[57] ABSTRACT

An article of headwear for covering the head, such as a hat, cap, or helmet, including coolant means for cooling the head of the wearer, and more particularly, cooling means which provide a prolonged cooling effect. The coolant means is contained in one or more pouches comprised of two layers of different materials, the first or outer material being a thin material having good thermal transmissive properties and preferably also having some water resistant properties, and the second or inner material provided interior of the first material and having thermal insulative properties. These layers, used in combination, have an effect of absorbing heat from the head of the wearer without at the same time absorbing excessive heat from the environment, and thus provide a sustained cooling effect. A heat releasing means can be substituted in place of the coolant means when it is desired to warm the head of the wearer.

17 Claims, 2 Drawing Sheets

HEADWEAR INCLUDING COOLANT MEANS

BACKGROUND OF THE INVENTION

1. Field of the Invention

The invention concerns headwear for covering the head, such as a hat or cap, including means for controlling the temperature of the head of the wearer. The headwear preferably includes coolant means in a specially constructed receptacle which prolongs the cooling effect.

2. Description of the Related Art

It is well known to provide pockets or enclosures in head gear for insertion of cooling materials. For example, U.S. Pat. No. 2,335,630 discloses a hat structure including a container adapted to receive dry ice or other refrigerant material.

U.S. Pat. No. 3,070,803 discloses a hat including a flexible water-impervious bag formed as part of the crown, the bag provided with an opening to allow the bag to receive and store a coolant in the form of a liquid or ice.

U.S. Pat. No. 3,090,045 teaches a thermal head appliance designed for holding a bag of ice in position on top of the wearer's head.

U.S. Pat. No. 4,484,363 teaches a hat in combination with a cooling device which is removably mounted to the front inside portion of the hat, the device including an enclosure defined by an inverted pocket adapted to receive and store a sealed container filled with a coolant to provide a cooling effect to the forehead and frontal portion of the wearer's head.

U.S. Pat. No. 5,054,122 teaches a hat with a cooling system for the head, the hat including a channel holder on its internal wall surface for receiving a plurality of cooling elements and a flexible, ventilating socket.

U.S. Pat. No. 5,197,292 discloses a headwear device comprising a hat having at least one chamber having a surface capable of transmission of fluid from the chamber to the interior surface of the cap. Melted ice water is permitted to travel to the scalp for cooling of the head.

U.S. Pat. No. 4,815,144 teaches a cap including a cooling pouch which contains a freezable liquid or gel inserted in the forehead area of the cap. The cooling pouch is formed to conform to the shape of the wearer's forehead and a plastic drain channel is provided to catch and retain any condensate which may form on the cooling pouch during periods of high humidity.

One problem with each of the above devices is that the cooling effect provided by the headgear is not sustained for a long period of time, particularly in high-heat conditions such as when repairing the roof of a building.

A further disadvantage of the above devices is that water condensation tends to form in the areas of the hat containing the coolant material, particularly during conditions of high humidity. This condensation represents an absorption of latent energy of atmospheric water vapor as the vapor is condensed into water. This absorption of energy from the atmosphere means that the coolant means is working to cool the atmosphere rather than the wearer, and thus means that (1) the cooling effect of the coolant means is not transmitted entirely to the wearer, and (2) the cooling means more rapidly warms to ambient temperature, so that the cooling effect is abbreviated.

A further problem with the prior art devices is that they may be adapted to receiving coolant means for cooling the head of the wearer when worn in high temperature conditions, but the same hat can not be used to receive heating means to heat the head of the wearer in low temperature conditions.

SUMMARY OF THE INVENTION

It is the object of the present invention to provide headwear including cooling means which provides cooling relief for a longer period of time than conventional headwear.

It is a further object of the present invention to provide headwear with cooling means which does not form condensation.

It is a further object of the invention to provide headwear including cooling means which eliminates or minimizes the above-mentioned and other problems, limitations and disadvantages associated with conventional headwear including cooling means, and to provide headwear with cooling means which is simple to manufacture, easy to use, inexpensive, reliable, attractive and which can be retrofitted to existing headwear such as caps.

It is a further object of the invention to provide headwear which is manufactured ready to receive a cooling means according to the present invention.

If is a further object of the invention to provide a kit for retrofitting existing conventional headwear.

Finally, it is an object of the invention to provide headwear which can provide extended cooling to the wearer particularly in conditions of high temperature and high humidity, and which can also receive heating means to heat the head of the wearer during low temperature conditions.

The foregoing has outlined rather broadly the more pertinent and important features of the present invention in order that the detailed description of the invention that follows may be better understood and so that the present contribution to the art can be more fully appreciated. Additional features of the invention, which will be described hereinafter, will form the subject of the claims of the invention. It should be appreciated by those skilled in the art that the conception and the specific embodiments disclosed may be readily utilized as a basis for modifying the disclosed headwear. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention reference should be made the following detailed description in conjunction with the accompanying drawings in which.

DESCRIPTION OF THE PREFERRED EMBODIMENTS

Figure 1:
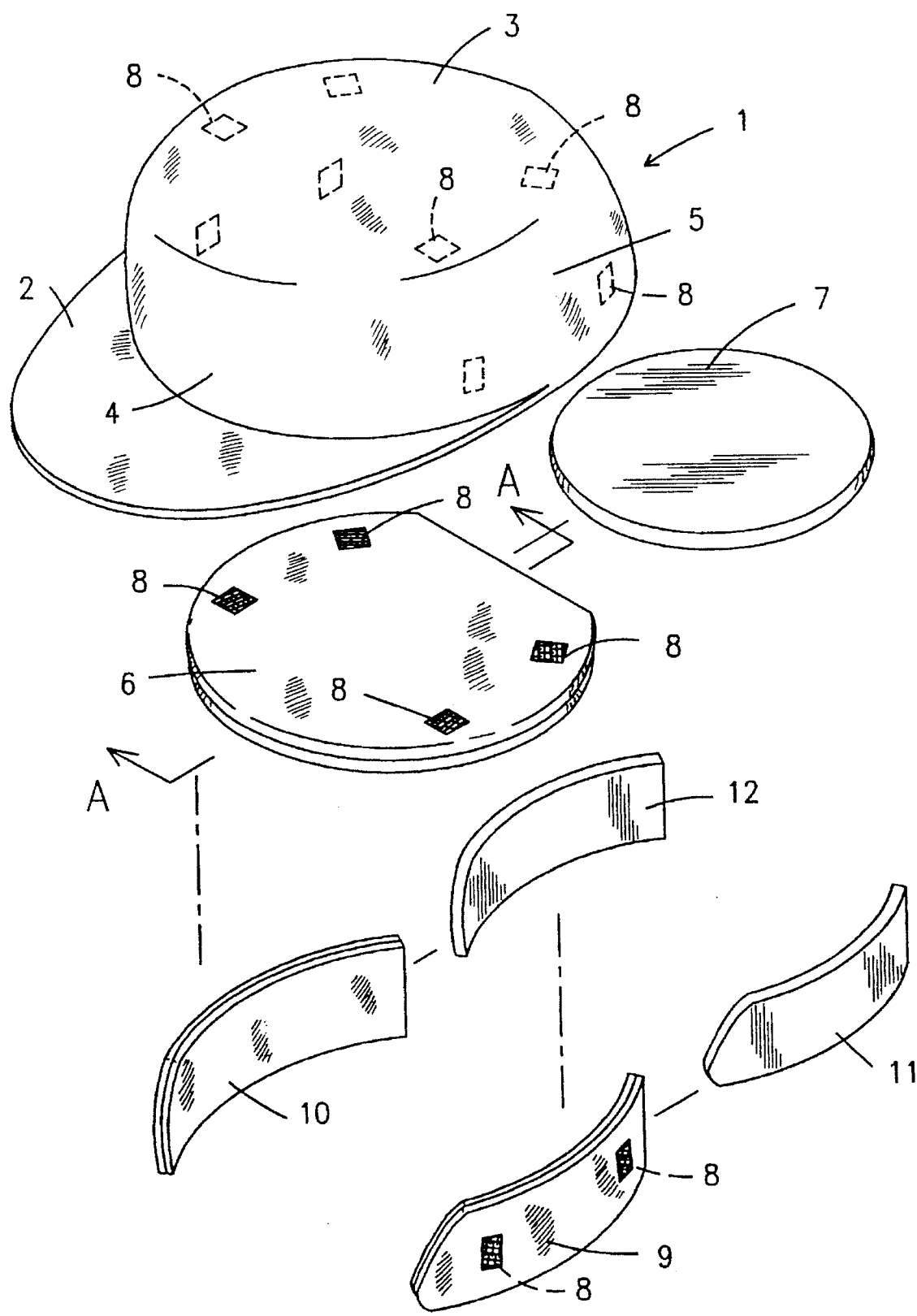
FIG. 1 shows a first embodiment of the headwear according to the present invention in exploded elevated perspective.

After extensive investigation and experimentation, the present inventor has discovered that the objects of the invention can be simply and inexpensively accomplished by an article of headwear having a shape adapted for covering at least the top, sides and front of the wearer's head, the top of the headwear provided with a pouch for receiving cooling means, the sides of the headwear provided with pouches for receiving cooling means, wherein said pouches are comprised of two layers of different materials, the first or outer material being a thin material having good thermal transmissive properties and preferably also having some waterproofing properties, and the second or inner material provided interior of the first material and having thermal insulative properties. The inner material is preferably at least one-eighth of an inch thick, and is preferably comprised of non-woven fibers. These layers, used in combination, have an effect permitting heat to be absorbed by the cooling pack from the head of the wearer without at the same time absorbing excessive heat from the environment, and thus provide a sustained cooling effect.

The inner, thermal insulative material preferably has a high void volume for providing insulation without weight, and may be foam rubber, felt, fleece or any sponge-like, soft, pliable material which protects the wearer's head from direct thermal contact with the coolant material and controls the rate of heat transfer from the wearer's head to the coolant material.

The outer material is preferably a water resistant or waterproof fabric or breathable plastic material which has an attractive appearance and is comfortable against the scalp of the wearer, and has the function of providing longevity and structural support, minimizing thermal transfer across the top of the headwear, and preventing moisture penetration into the vicinity of the coolant means.

In a further preferred embodiment the headwear (FIG. 3) is provided with an additional pouch extending along the back of the head, which pouch is water-transmissive, said pouch constructed for receiving ice which can melt and drip down the back of the head of the wearer. This cooling means at the back of the head preferably also includes a sheet of fabric for covering the neck of the wearer. This sheet helps to cool the head in two ways: first by providing shade, and second by providing evaporative cooling as ice melts from the pouch at the back of the head and water slowly drips and flows by gravity down the back of the head and neck of the wearer.

The headwear which contains the cooling means according to the present invention may be any of the conventional lightweight, sun-proof headwear having good heat insulating and tear-resisting properties. The headwear preferably protects the entire head from the radiant heat of the sun, while the cooling means absorbs heat from the head of the wearer and thereby reduces body heat so that it is not necessary to cool other parts of the body at the same time. The combination headwear and cooling means establishes a comfortable condition even when the wearer is exposed to intensive sun during outdoor activities.

The materials used in the construction of the headwear are now discussed in greater detail.

The cooling means are not particularly limited, and may be any of the reusable cooling means conventionally employed in this art, in the health care (physical therapy) art, in the food cooling art, etc. The cooling means are preferably sealed bags made of a flexible plastic material having a refreezable liquid or semi-liquid material enclosed therein, which bags can be readily removed from the pouch and placed in a freezer for cooling or refreezing of the coolant so as to be ready for use again when needed. It is not necessary to place the entire headwear with coolant bags into a freezer during the cooling or refreezing process.

As a specific example of such a cooling pack, see U.S. Pat. No. 3,545,230 or the water/propylene glycol/hydroxypropyl methylcellulose gel pack marketed by 3-M Company under the trademark "COLD COMFORT"

An advantage of providing removable cooling means is that the when the environmental condition does not require the additional cooling means, the cooling means can be removed from the headwear and the headwear be worn as a conventional hat or cap. Then, as the temperature becomes very low, heating means can be inserted in place of the cooling means.

Turning now to heating means, a wide variety of chemical heating means may be employed in place of the cooling means. The heating means are conventionally referred to as "hot packs", may be of two types.

One type of hot pack is based upon an exothermic chemical reaction employing anhydrous calcium chloride, anhydrous sodium sulfate, and a solution consisting of anhydrous sodium acetate and water, as disclosed in U.S. Pat. No. 4,203,418. These chemicals are contained in a package comprising an outer and an inner container, the sealed, flexible, impermeable, water insoluble outer enclosure containing a liquid material and a sealed, flexible, impermeable, water insoluble inner enclosure having low resistance against rupture and puncture and containing a second liquid. The hot pack is activated when the inner enclosure is ruptured. This type of hot pack is not reusable, but can be readily removed from the pouch according to the present invention.

A further type of heat pack is the type which reacts with air (oxygen) as disclosed in, e.g., U.S. Pat. No. 4,756,299, 5,230,333 and 5,302,806, and the product known as MEDIHEAT™ or HOTHANDS-2™ produced by Heat-max, Inc. of Dalton, Ga. Such heat packs can release heat for up to 6 hours.

For sustained heat of 122° F. for up to 20 hours (e.g., military helmets, motorcycle or bicycle helmets, hunters), a pack containing iron powder, water, vermiculite, activated charcoal and salts as disclosed in RE32,026 is preferred.

Other heat releasing packs include FOOT WARMER manufactured in Taiwan for K-Mart Corporation of Troy, Mich. and GRABBER™ manufactured by Mycoal Warmers Co., Ltd. of Japan.

It is also possible to use packs which can be used to release heat or cold, as disclosed in U.S. Pat. Nos. 3,804,077, 4,462,224 and 5,069,208. Such heat/cold packs can be used in summer for cool and in winter for heating.

Turning now to the inner layer of the pouch, the thermal insulative material, examples of such materials and methods of adhering them to a cover material layer are disclosed, for example, in U.S. Pat. No. 5,295,267. A protective loincloth garment for motorcyclists is composed of a wind and weather resistant outer surface and a comfortable and insulating inner surface, such as fleece. These surfaces are bonded together by a flexible, temperature and water resistant cement, glue or adhesive (best illustrated in FIG. 3 of U.S. Pat. No. 5,295,267). For added durability, decorative or simple rivets may be used to further secure the outer and inner surfaces together.

In the case that the pouch is to be used with heating means, the inner, thermal insulative material preferably has a high void volume for providing insulation without weight, a high pile fabric with air-trapping qualities, and may be fleece or any soft, pliable material which protects the wearer's head for direct contact with the heating material, controls the rate of heat transfer from the wearer's head, and diffuses the heat supplied by the heating material.

Further examples of fleece type materials are shown in U.S. Pat. No. 5,236,770, disclosing a textile laminate consisting of a nonwoven padding material of low specific volume and of a filament-reinforced nonwoven material. The nonwoven padding material has a raw density of less than 0.025 g/cm³ and a thickness of 1.6 to 60 mm. The filament-reinforced nonwoven material is composed to 10 to 60 g/mof a fleece with a raw density greater than 0.35 g/cm³ and of 3 to 10 g/mreinforcing filament and is laminated onto the nonwoven padding material.

U.S. Pat. No. 5,230,922 discloses bonding of lightweight fleeces. U.S. Pat. No. 5,214,804 discloses an article of clothing formed of a closed-cell neoprene with a fleece interior lining and a LYCRA exterior surface. U.S. Pat. No. 5,063,101 discloses a textile product and a method for making that product formed of a bonded base material having bonded thereon a fleece of adhesive fibers, which can be fused to a shirt fabric such as a broadcloth.

Methods of producing natural and synthetic fleece and for adhering fleece to other materials are disclosed in U.S. Pat. Nos. 5,032,329, 5,028,375, 4,838,774, 4,679,278, 4,658, 477, 4,651,386, 4,632,858, 4,025,254, 4,019,350, 3,997,928, 3,961,107, 3,798,298, 3,764,450, 3,723,238, 3,680,561, 3,621,531, 3,471,315.

Turning now to the outer material layer, this material is preferably the same material as the coated fabrics and fabric laminates used in the fabrication of tenting, rainwear and other garments where water resistance or waterproofness, coupled with breathability, are important features. Examples of suitable materials are disclosed in U.S. Pat. Nos. 5,283, 112 and 5,239,037, which disclose waterproof breathable polyurethane compositions specifically adapted to produce non-porous membranes exhibiting waterproof and water vapor transmissible characteristics. The membranes can be produced as free standing products or can be produced as coatings on porous substrates to confer similar properties to such substrates. Also disclosed are coated fabrics and fabric laminates utilizing the membranous coatings and exhibiting waterproof and water vapor transmissible characteristics.

Further materials are those used in U.S. Pat. No. 5,271, 659 which discloses a portable seat constructed of a thin, lightweight, shell of GORTEX material which is then lined with THINSULATE material or some similar heat retaining fabric. This combination of cover and insulation may satisfy the requirements of the outer and inner material layers of the present invention.

U.S. Pat. No. 5,204,403 discloses a water-vapor permeable, waterproof coated fabric having a fibrous base fabric, and a porous film coated on one side of the base fabric. The porous film comprises a synthetic polymer composed mainly of a polyurethane resin and inorganic fine particles having a mean particle diameter of not more than 0.1 μm. In the porous film, microcells intercommunicate in the thicknesswise direction of the film to form a honeycomb skin core structure having a diameter of 1 to 20 μm. The porous film has a multiplicity of micropores having a diameter of not more than 1 μm. The coated fabric has waterproof and water-vapor permeability characteristics sufficient to meet such performance characteristics required in various applications, such as rainwear, military garments, and sportswear. This combination of cover and insulation may satisfy the requirements of the outer and inner material layers of the present invention.

Methods of joining the materials or fabrics are disclosed in U.S. Pat. No. 5,123,119, concerning a breathable glove. A homogeneous membrane in regard to its permeability characteristics is attached to a fabric. The membrane is tacky on one surface and wear resistant on the other surface. Using a contoured mold and foam forms the layers for the inner liner are cut and are thermowelded or bonded together to form a three dimensional inner shell of a glove. Then the formed inner shell is attached to an outer glove shell by conventional methods.

As a further teaching of a method of construction, see U.S. Pat. No. 5,095,718 which teaches a compartmentalized refrigeration case for cans of beverage and/or food. The refrigeration compartments in the interior of the case are formed by at least one layer of thermoplastic coated, multi-layer panels comprised of a thermally insulating and supportive foam sandwiched between an inner lining of waterproof material and an outer covering of water-resistant, durable fabric. The materials used in the construction of this case could be used for the construction of headwear according to the present invention.

U.S. Pat. No. 5,074,300 discloses a reusable, fabric-covered heat exchange bag including a thermoplastic waterproof liner means having an interior containment area and an opening for receiving a hot or cold medium, such as hot water or ice.

Further examples of materials and methods of joining materials are disclosed in the following U.S. Patents, the disclosures of which are incorporated herein by reference:

| | |
|---|---|
| 4983450 | GAS-PERMEABLE, WATERPROOF NONWOVEN FABRIC AND PROCESS FOR ITS PRODUCTION |
| 4895751 | WATERPROOF, WATER-VAPOR-PERMEABLE FABRIC CONSTRUCTION |
| 4869952 | WATERPROOF SHELTER FABRIC |
| 4803116 | WATERPROOF FABRIC HAVING HIGH MOISTURE PERMEABILITY AND METHOD OF MAKING SAME |
| 4636424 | MOISTURE-PERMEABLE WATERPROOF LAMINATED FABRIC AND PROCESS FOR PRODUCING THE SAME |
| 4632860 | WATERPROOF BREATHABLE FABRIC |
| 4560611 | MOISTURE-PERMEABLE WATERPROOF COATED FABRIC |
| 4539255 | MOISTURE-PERMEABLE WATERPROOF FABRIC |
| 4537817 | WATERPROOF FABRIC AND FABRICATION METHOD THEREOF |
| 4535008 | MOISTURE-PERMEABLE WATERPROOF COATED FABRIC HAVING A MICROPOROUS POLYURETHANE LAYER |
| 4454191 | WATERPROOF AND MOISTURE-CONDUCTING FABRIC COATED WITH A HYDROPHILIC POLYMER |
| 4429000 | MOISTURE-PERMEABLE WATERPROOF COATED FABRIC AND METHOD OF MAKING THE SAME |
| 3932682 | AIR PERMEABLE WATERPROOF PRODUCTS HAVING |

| | |
|---|---|
| | FABRIC-LIKE AESTHETIC PROPERTIES AND METHODS FOR MAKING THE SAME |
| 3690977 | METHOD FOR MAKING AIR-PERMEABLE WATERPROOF PRODUCTS HAVING FABRIC-LIKE AESTHETIC PROPERTIES |
| 3675391 | BREATHABLE WATERPROOF FABRIC |
| 3506734 | WATERPROOF COATING COMPOSITION FOR POLYESTER TYPE FABRIC |
| 34818821 | WATERPROOF FABRIC AND METHOD FOR FORMING THE SAME |

The invention will now be discussed in greater detail with respect to a specific embodiment as shown in FIG. 1. FIG. 1 shows a cap 1 of conventional design. The headwear of the present invention may be any desired shape or configuration or construction, and may include such diverse headwear as motorcycle helmets, construction hard-hats, safety helmets, military helmets, bicycling helmets, cowboy hats, etc.; however, a cap illustrate how any headwear can be readily adapted to receive the cooling means according to the present invention.

The cap is comprised of a visor 2 and a crown comprising an upper area generally indicated by 3, a front area generally indicated by 4, and side areas indicated by 5. Pouch 6 is adapted for receiving cooling means 7. Pouch 6 and cooling means 7 are tailored for attachment to the upper portion of the cap 3. In the case where pouch 6 is not permanently attached to cap 1 by means such as rivets or waterproof glue, pouch 6 may be attached to cap 1 by zipper means, VELCRO hook-and-pile fastener 8, snap fasteners, etc.

Pouches 9, 10 and cooling means 11, 12 are constructed to be attached to the left and right sides of the cap, and one or both may extend to the front or forehead area of the cap. In one embodiment of the invention, pouches 9, 10 and cooling means 11, 12 are constructed so as to cover only the left and right sides of the cap. In a variation of this embodiment one or both of these pouches are increased in length so as to cover the temple portion of the head. In a further variation, the pouches are extended to cover the rear portion of the head.

Figure 2:
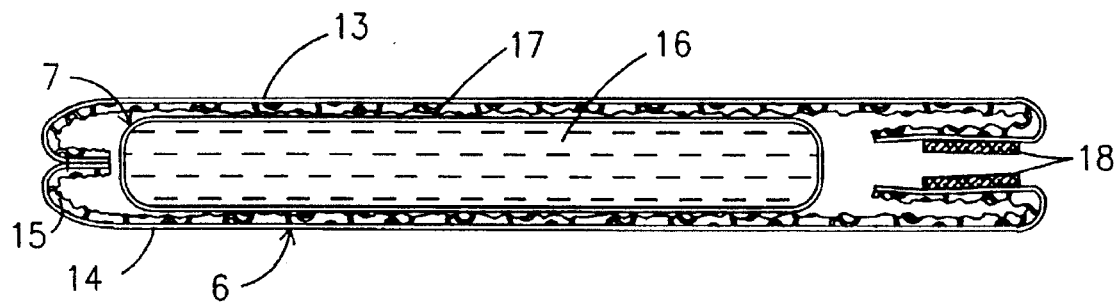
FIG. 2 shows a cross-sectional view of a pouch containing cooling means across line A—A.

FIG. 2 shows the cooling means as inserted in a pouch. Cooling means include a coolant 16 and sealed bag or container 17 which may be comprised of a water-impermeable material such as plastic. The bag or container 17 is filled with a liquid or semiliquid gel-like substance 16. An example of the widely available conventional coolants is a coolant liquid produced by the 3-M Company, which coolant will not completely freeze under normal freezer conditions and temperatures. Thus, when the coolant is stored in a freezer for a period of time it forms a permanent pliable slush which will not freeze to a hard state such as ice. The material remains sufficiently pliable to be inserted into the packets and to conform to the head of the wearer.

The pouch is comprised of an outer layer of material 13 which faces away from the head of the wearer and an inner material 14, 15. The inner material is a sponge or foam or fleece-like material having a high insulating value and high void volume and is selected so as to permit coolant 16 to absorb heat given off by the head of the wearer, but not to cause the surface layer to cool to the point of causing significant condensation on outer layer 13, 14.

One outer layer of material 14 is provided between the coolant insulating layer 15 and the head of the wearer, and another outer layer of material 13 is preferably also provided on the opposite side of the pouch. This outer layer of material 14 may be the same material as layer 13; however, layer 14 it is designed mainly for the improvement of comfort and durability since the material of layer 15 is not selected for strength or durability characteristics. Layer 13 is a material characterized by good insulation value while at the same time being lite, thin and pliable, and preferably water resistant or waterproof.

Once the cooling packet is inserted in the pouch, the pouch can be sealed by snap fasteners, zippers, or VELCRO hook-and-pile fastener 18 as shown in FIG. 2.

Figure 3:
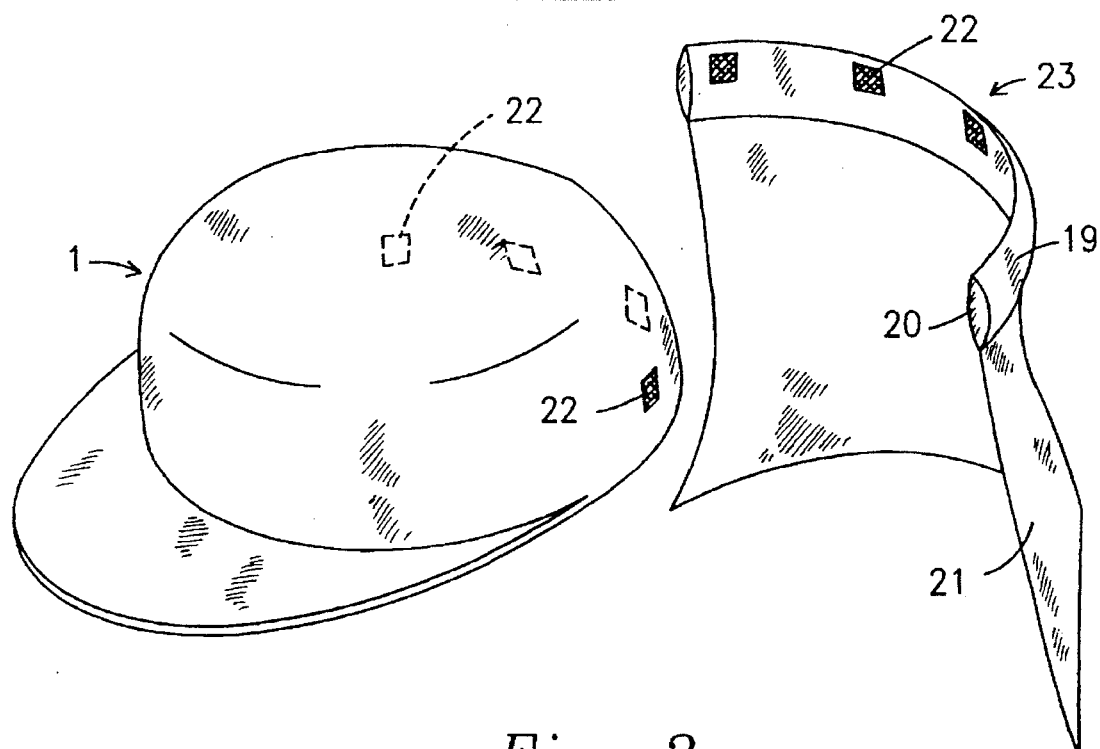
FIG. 3 shows a second embodiment of the invention.

A further refinement of the head cover of the present invention is shown in FIG. 3. In FIG. 3, cap 1 is provided with an additional element generally indicated by 23 comprising a pocket 19 including an opening 20 into which ice can be introduced. As the ice melts, water drips down the sheet 21 to cool the back of the head and neck of the wearer. This additional element can be attached to the inside of the back of the cap by VELCRO hook-and-pile fastener 22.

In a yet further modification of the invention, a sheet of material such as a highly reflective metal foil as used in "space blankets" can be included in the hat between the cooling packet 16, 17 and the roof of the cap 3. This layer would help reflect solar heat away from the cooling packet, and would help keep the cooling packet cooler longer.

Although the present invention was first designed for retrofitting less expensive to moderately expensive hats, it will be readily apparent that the system is capable of application to more expensive hats such as cowboy hats, and to the production of hats with removable, washable, and reusable hat pockets in place. The invention may be in the form of a kit by which the end user can retrofit his own hat, or may be in the form of individual elements by means of which a retailer, for example, a shoe repair shop, can retrofit hats. Finally, the system can be used to provide new hats with the system already in place.

Furthermore, the system can be used to modify a hat or cap which is not originally intended to be fitted with a cooling means, such as a motorcycle helmet. For a motorcycle helmet, it is merely necessary that pockets of styrofoam insulation be replace with coolant packs of the present invention.

The invention thus capable of use in a number of other applications. Although this invention has been described in its preferred form with a certain degree of particularity with respect to a cooling means for a cap, it is understood that the present disclosure of the preferred form has been made only by way of example and that numerous changes in the details of structures and the composition of the system may be resorted to without departing from the spirit and scope of the invention.

Now that the invention has been described,

What is claimed is:

1. An article of headwear having coolant means removably supported therein, comprising:

headwear having at least a crown section designed to cover the top of a head of a wearer, said crown section including at least a dome, front, and left and right sides;

at least one pouch secured inside said crown, said coolant means comprising a pliable closure means containing a liquid adapted to be refreezable, said coolant means shaped to be received and stored in said pouch;

wherein said pouch is constructed of a first layer of a first material and a second layer of second material, said second material different from said first material, said first layer of material provided on the outside of said pouch and being a thin material having good thermal transmissive properties, and said second material provided interior of said first material and having thermal insulative properties.

2. An article of headwear as in claim 1, wherein said pouch is removably secured inside said headwear to the dome of said crown section of said headwear, said securing means being arranged to cause said pouch to conform to the configuration of said crown section of said headwear, such that said coolant means is positioned on top of the head when said headwear is worn.

3. An article of headwear as in claim 1, wherein said headwear further comprises second and third pouches and second and third coolant means, said coolant means containing a liquid adapted to be refreezable to a thixotropic and pliable state, said coolant means shaped to be received and stored in said pouches, and wherein said pouches are attached to the left and right inside sides of the crown.

4. An article of headwear as in claim 3, including means for removably securing said left side pouch to the left side of said crown of said headwear, said securing means being arranged to cause said left side pouch and said coolant means therein to conform to the configuration of said left side of said headwear, whereby said coolant means is positioned on the left side of the head when said head wear is worn; and means for removably securing said right side pouch to the right side of said crown of said headwear, said securing means being arranged to cause said right side pouch and said coolant means therein to conform to the configuration of said right side of said headgear, whereby said coolant means is positioned on the right side of the head when said headwear is worn.

5. An article of headwear having coolant means removably supported therein, comprising:

headwear having at least a crown section designed to cover the top of a head of a wearer, said crown section including at least a dome, front, and left and right sides;

at least one pouch secured inside said crown;

said coolant means comprising a pliable closure means containing a liquid adapted to be refreezable said coolant means shaped to be received and stored in said pouch;

wherein said pouch is constructed of a first layer of a first material and a second layer of a second material said second material different from said first material, said first layer of material provided on the outside of said pouch and being a thin material having good thermal transmissive properties and said second material provided interior of said first material and having thermal insulative properties, and wherein said first layer of a first material provided on the outside of said pouch is a water resistant fabric of a breathable synthetic material.

6. An article of headwear as in claim 1, wherein said headwear is a motorcycle helmet.

7. An article of headwear as in claim 1, wherein said second material provided interior of said first material and having thermal insulative properties is a foam rubber.

8. An article of headwear as in claim 1, wherein said second material provided interior of said first material and having thermal insulative properties is fleece.

9. An article of headwear as in claim 1, wherein said second material provided interior of said first material and having thermal insulative properties is felt.

10. An article of headwear as in claim 1, wherein said pouch is secured to said crown by means of a plurality of snap fasteners.

11. An article of headwear as in claim 1, wherein said pouch is adapted to receive a heat pack.

12. An article of headwear as in claim 1, wherein said pouch is secured to said crown by means of hook and pile fasteners.

13. An article of headwear as in claim 1, wherein said coolant means comprises a sealed container formed from a thin, pliable, water-impermeable material, said container being formed having a substantially circular configuration.

14. An article of headwear as in claim 1, wherein said headwear further comprises a pouch adapted to contain ice and having a surface comprising a water-transmissive means allowing melted ice to drip slowly onto a head of the wearer, said pouch being removably attached to the back of the crown of said headgear, said pouch further provided with a section of material to cover the neck of the wearer.

15. An article of headwear as in claim 14, wherein said pouch is removably attached by means of hook-and-pile fasteners.

16. An article of headwear having coolant means removably supported therein, comprising:

headwear having at least a crown section designed to cover the top of a head of a wearer, said crown section including at least a dome, front, and left and right sides;

at least one pouch secured inside said crown, said pouch adapted for alternatively receiving a coolant means and a heating means, said coolant means containing a liquid adapted to be refreezable, said heating means releasing heat upon activation, said coolant means shaped to be received and stored in said pouch;

wherein said pouch is constructed of a first layer of a first material and a second layer of material different from said first material, said first layer of material provided on the outside of said pouch and being a thin material having good thermal transmissive properties, and said second material provided interior of said first material and having thermal insulative properties.

17. A kit for modifying an article of headwear to provide cooling or heating, said article of headwear comprising at least a crown section designed to cover the head of the wearer, said crown section including at least a dome, front, and left and right sides, and said kit comprising:

at least one pouch adapted for alternatively receiving a coolant means and a heating means;

means for securing said pouch to the inside of the dome of said headwear;

coolant means containing a liquid adapted to be refreezable to a thixotropic and pliable state and shaped to be received in said pouch;

wherein said pouch is constructed of a first layer of a first material and a second layer of material different from said first material, said first layer of material provided on the outside of said pouch and being a thin material having good thermal transmissive properties, and said second material provided interior of said first material and having thermal insulative properties.

* * * * *